| | | | |
|---|---|---|---|
| | | |  |

United States Patent [19]

Lizardi

[11] Patent Number: 5,782,864
[45] Date of Patent: Jul. 21, 1998

[54] KNOTLESS SUTURE SYSTEM AND METHOD

[75] Inventor: José E. Lizardi, Franklin, Mass.

[73] Assignee: Mitek Surgical Products, Inc., Westwood, Mass.

[21] Appl. No.: 825,760

[22] Filed: Apr. 3, 1997

[51] Int. Cl.⁶ ............................................. A61B 17/04
[52] U.S. Cl. ...................... 606/232; 606/224; 606/215; 606/72; 606/75
[58] Field of Search ........................ 606/232, 60, 72, 606/73, 74, 75, 148, 215, 224

[56] References Cited

U.S. PATENT DOCUMENTS

| | | | |
|---|---|---|---|
| 5,123,913 | 6/1992 | Wilk et al. | 606/232 |
| 5,129,912 | 7/1992 | Noda et al. | 606/139 |
| 5,152,769 | 10/1992 | Baber | 606/145 |
| 5,178,629 | 1/1993 | Kammerer | 606/224 |
| 5,226,535 | 7/1993 | Rosdhy et al. | 206/363 |
| 5,259,846 | 11/1993 | Granger et al. | 606/224 |
| 5,282,809 | 2/1994 | Kammerer et al. | 606/148 |
| 5,320,629 | 6/1994 | Noda et al. | 606/139 |
| 5,534,011 | 7/1996 | Greene, Jr. et al. | 606/232 |
| 5,569,306 | 10/1996 | Thal | 606/232 |

*Primary Examiner*—Michael Powell Buiz
*Assistant Examiner*—Tina T. D. Pham
*Attorney, Agent, or Firm*—Nutter, McClennen & Fish, LLP

[57] ABSTRACT

A system for anchoring tissue to bone includes a suture anchor, a first loop of suture thread attached to the suture anchor, a suture needle and a second loop of suture thread which is attached to the suture needle, the first and second suture loops are interlocked with one another. The suture needle can be of a conventional type useful in open surgical procedures, or a type useful in closed surgical procedures that is formed on the end off an elongate tool. A method for anchoring soft tissue to bone using the system is also provided.

23 Claims, 8 Drawing Sheets

KNOTLESS SUTURE SYSTEM AND METHOD

FIELD OF THE INVENTION

The invention relates to a knotless suture system for attaching soft tissue to bone and to methods for attaching soft tissue to bone.

BACKGROUND OF THE INVENTION

Soft tissues, such as ligaments, tendons and muscles, are attached to a large portion of the human skeleton. In particular, many ligaments and tendons are attached to the bones which form joints, such as shoulder and knee joints. A variety of injuries and conditions require attachment or reattachment of a soft tissue to bone. For example, when otherwise healthy tissue has been torn away from a bone, surgery is often required to reattach the tissue to the bone to allow healing and a natural reattachment to occur.

A number of devices and methods have been developed to attach soft tissue to bone. These include screws, staples, cement, suture anchors, and sutures alone. Some of the more successful methods involve use of a suture anchor to attach a suture to the bone, and tying the suture in a manner that holds the tissue in close proximity to the bone.

The tissue may be attached to the bone during open surgery, or during closed (e.g., arthroscopic) surgical procedures. Closed surgical procedures are preferred since they are less invasive and are less likely to cause patient trauma. In a closed surgical procedure, the surgeon performs diagnostic and therapeutic procedures at the surgical site through small incisions, called portals, using instruments specially designed for this purpose. One problem encountered in the less invasive, closed surgical procedures is that the surgeon has significantly less room to perform the required manipulations at the surgical site. Thus, devices and methods are needed which will allow a surgeon to effectively and easily attach tissue to bone in the small spaces provided by less invasive surgical procedures.

Conventional methods for attaching soft tissue to bone typically require that the surgeon tie a knot in the suture thread to attach the suture to an anchor, or to attach the tissue to the bone using the suture. Knot tying at the surgical site in closed surgical procedures, and even in open surgery, is difficult and time consuming due to inherent space constraints. Further, knots and other bulky attachment means can irritate tissue over time.

Knotless suture anchor systems have been developed for use with closed surgical procedures, and U.S. Pat. No. 5,569,306 provides one example of such a system. Although generally useful, such systems can be limited to use only with certain types or shapes of tissue, or to use with certain anatomical structures. Proper attachment of soft tissue requires that it be placed in the anatomically correct position to promote optimal healing.

Alternatively, conventional knotless suture anchor systems may require, in order to attach a broader array of tissue shapes to bone, that the suture anchor pass though the tissue to be attached. This is undesirable because it unnecessarily irritates the injured tissue and it requires opening a much larger hole in the tissue.

There is thus a need for an improved system for anchoring soft tissue to bone which reduces or eliminates the need to tie suture knots at the surgical site.

SUMMARY OF THE INVENTION

The present invention provides a system for anchoring tissue to bone including a suture anchor, a first suture loop attached to the suture anchor, a suture needle and a second suture loop attached to the suture needle and interlocked with the first suture loop. The second suture loop may be formed by attaching two free ends of a length of suture thread directly to the suture needle, or by attaching the two free ends within a suture closure which may then be attached to the suture needle. A method is also provided by which a detached tissue may be securely attached to bone in an anatomically correct position without the need to tie a knot.

In an exemplary embodiment, the system includes a substantially cylindrical suture anchor having opposed deformable barbs. The first suture loop is attached to a trailing end of the suture anchor and is interlocked with the second suture loop. The second suture loop is attached to a trailing end of the suture needle.

In an embodiment that is particularly useful in closed surgery, the second suture loop is formed using a suture loop closure and is attached to a hollow suture needle by means of a slot provided in a wall of the hollow needle. This embodiment may also employ an actuator, disposed within the hollow needle, which can be selectively deployed to disengage the second suture loop from the needle. The hollow needle used with this embodiment preferably is part of an elongate tool, such as a suture inserter, that is useful in closed surgical procedures. The hollow needle typically forms the distal end of such a tool.

The system may be used in a method wherein the suture needle and the attached second suture loop are passed through a detached segment of tissue. The second suture loop is pulled through the detached tissue until a portion of the interlocked first suture loop extends through the detached tissue. The suture anchor is then passed through the portion of the first suture loop which extends though the detached tissue and into a preformed bore in the bone to which the detached tissue is to be secured. The detached tissue is thereby attached to the bone in the desired position.

The term "suture needle" is used herein to encompass both conventional suture needles, used in open surgical procedures, as well as suture needles that may form a hollow, distal end of an elongate tool useful with closed surgical procedures.

Further features of the invention, its nature and various advantages, will be more apparent from the accompanying drawings and the following detailed description of the drawings and the preferred embodiments.

DETAILED DESCRIPTION OF THE INVENTION

Figure 1:
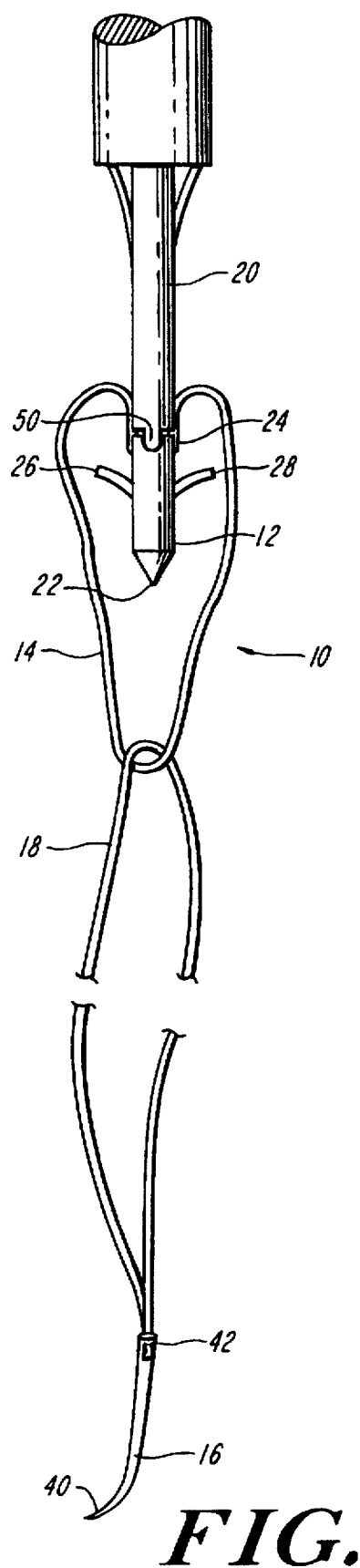
FIG. 1 is an elevated view of an exemplary suture anchor system of the invention.

Referring now to FIG. 1, a system 10 for anchoring tissue to bone in accordance with the invention is shown. The system includes a suture anchor 12, a first suture loop 14 attached to the suture anchor 12, a suture needle 16 and a second suture loop 18 attached to the suture needle 16. The first suture loop 14 and the second suture loop 18 are interlocked with each other. The system may also include an anchor insertion tool 20.

The suture anchor 12 has a first, bone penetrating end 22 and a second trailing end 24. In the exemplary embodiment shown in FIG. 1, the suture anchor 12 is substantially cylindrical in shape and the first end 22 forms an apex. The exemplary suture anchor 12 additionally comprises two opposed deformable barbs 26, 28 extending from a side wall of the suture anchor 12. More or fewer deformable barbs may be provided as desired to ensure proper retention of the suture anchor 12 within a bone. As further shown in FIG. 1, the deformable barbs 26, 28 may extend toward the second end 24 such that each barb defines an angle with a longitudinal axis of the anchor member that is between about 10° and 90°, and preferably about 30°. It will be understood that other suture anchor configurations may be used consistent with the practice of the invention.

The first suture loop 14 may be suitably attached to the suture anchor 12 through a hole or holes provided in the body of the suture anchor 12 or by a suture retaining slot formed within the body of the suture anchor 12. In the exemplary suture anchor 12, the first suture loop is attached in proximity to the second end 24 of the suture anchor 12 and portions of first suture loop 14 extend past the second end 24 on opposed sides of the suture anchor 12. Grooves (not shown), suitable for seating portions of the first suture loop 14, may be provided in the suture anchor 12 extending from the point of attachment of the first suture loop 14 to the second end 24.

Figure 2:
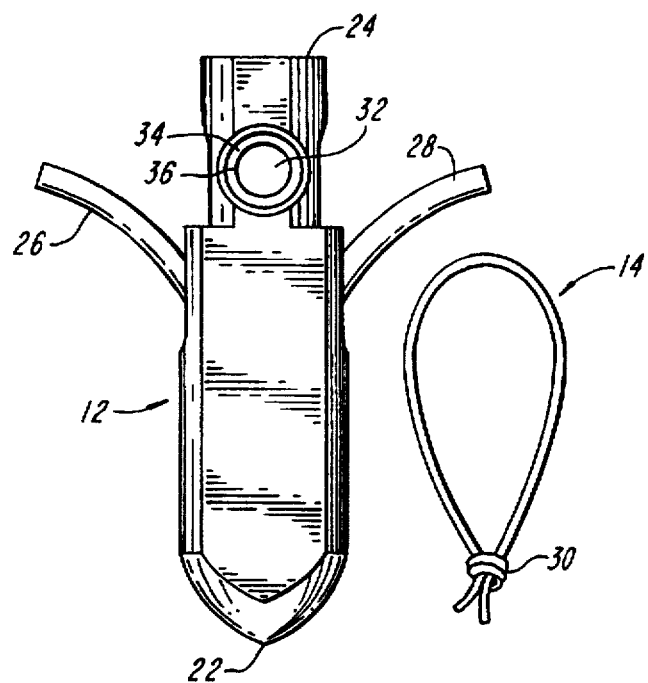
FIG. 2 is a view of a suture anchor and a separate first suture loop.
Figure 3:
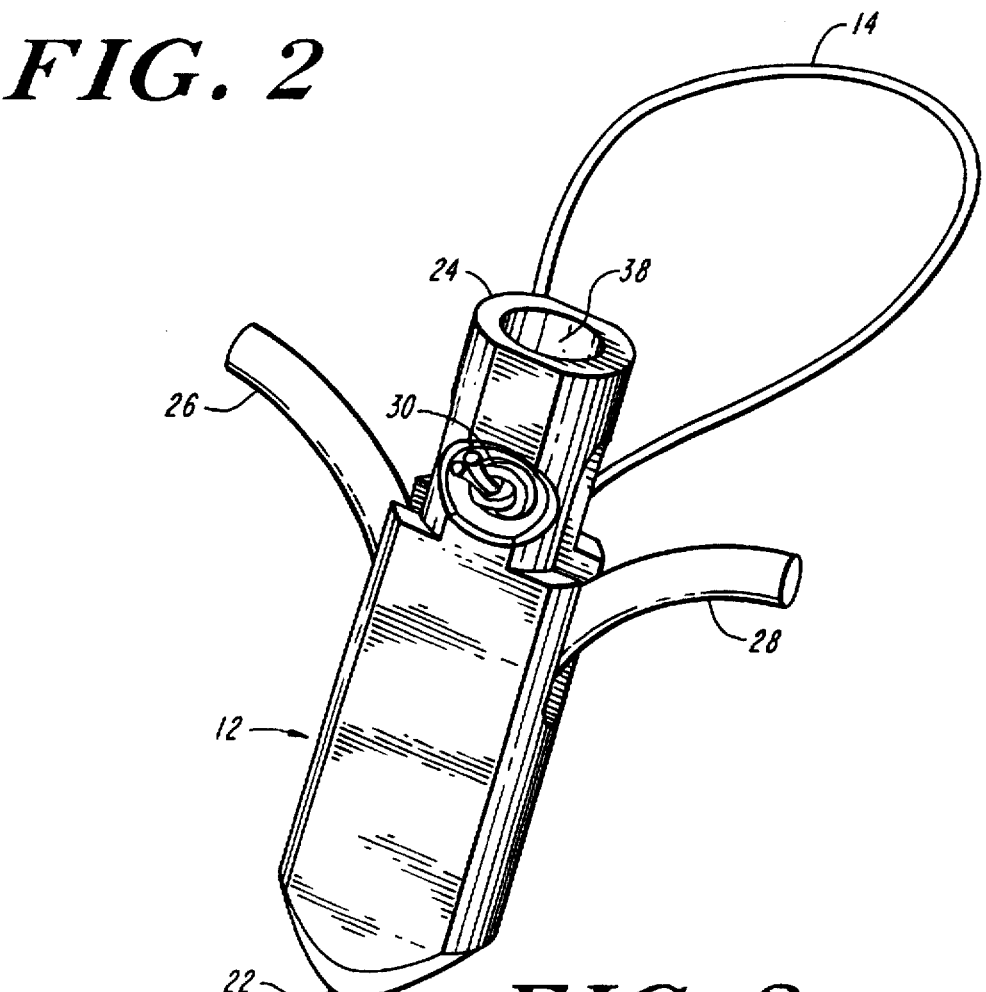
FIG. 3 is a view of the first suture loop of FIG. 2 engaged with the suture anchor of FIG. 2.

In an additional embodiment, the first suture loop 14 may be attached to the suture anchor 12 as illustrated in FIGS. 2 and 3. In FIG. 2, the first suture loop 14 is shown separate from the suture anchor 12. The first suture loop 14 is formed from a length of suture thread by tying the two free ends of the thread into a knot 30. It will be understood that other methods of attaching the two free ends, including the use of suture loop closure devices as further described below with regard to the second suture loop, may be used.

The suture anchor 12 of FIG. 2 is provided with a through-hole 32 proximate to the second end 24. The hole 32 is adapted, by providing varying diameters within the hole 32, to retain the first suture loop 14. In the embodiment shown in FIG. 2, the diameter within the hole 32 is varied by providing an annular collar 34 therein. The inner diameter 36 of the annular collar 34 is large enough to allow the unknotted portion of the first suture loop 14 to pass through the inner diameter 36. The inner diameter 36 is small enough, however, to prevent the knot 30 from passing through the hole 32. When the unknotted portion of the first suture loop 14 is drawn through the hole 32, as illustrated in FIG. 3, the knot 30 is retained by the annular collar 34 and the first suture loop 14 is thereby attached to the suture anchor 12.

As can further be seen by reference to FIG. 3, the second end 24 of the suture anchor 12 may be provided with a mating feature 38 for mating the suture anchor 12 to the anchor insertion tool 20. As illustrated, the mating feature 38 is a bore formed in the second end 24 of the suture anchor 12. Other configurations may be used as required.

The first suture loop 14 may be constructed from thread suitable for use as a suture. A variety of suture materials are well known to those of ordinary skill in the art. Exemplary materials include braided polyester and polydioxanone (PDS).

The length of the first suture loop 14 may be determined by a person of ordinary skill in the art depending upon the specific application of the system. This dimension depends, to a large extent, upon the dimensions of the tissue to be attached, the type of surgery to be performed, and whether an open or closed surgical technique is to be used. By way of example, the length of the first suture loop may range from about one quarter to one and one half inches in procedures to repair a Bankart lesion or a rotator cuff tear. In an exemplary embodiment as used in the method described hereinbelow, the length of the first suture loop 14 is about one half inch.

Referring again to FIG. 1, the suture needle 16 has a first, tissue penetrating end 40 and a second trailing end 42. The size and shape of the needle used with the system of the invention may be selected by a person of ordinary skill in the art depending upon the specific application of the system, and in particular, depending upon whether the system is used in an open or closed (e.g., arthroscopic) surgical procedure. Generally, needle 16 is at least slightly curved.

In the exemplary embodiment of FIG. 1, which is typically used in open surgical procedures, the second suture loop 18 is attached to the suture needle 16 at the second end 42 of needle 16. One of ordinary skill in the art will appreciate that a number of techniques can be utilized to join the second suture loop 18 to the suture needle 16. For example, the second end 42 of the suture needle 16 can be hollowed so that two free ends of suture thread may be inserted therein. The hollowed end is then crimped to securely retain the two ends of suture thread within the second end 42 of the needle 16, thus creating the second suture loop 18.

Figure 4:
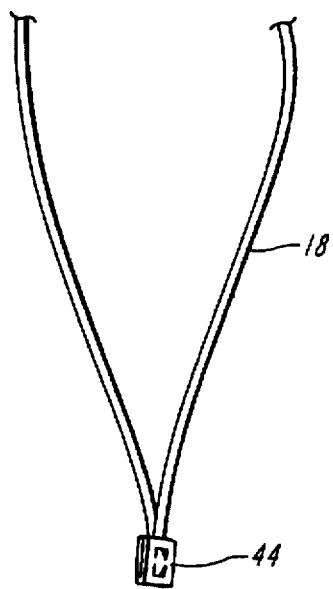
FIG. 4 is a partial view of a second suture loop with a suture loop closure.
Figure 5:
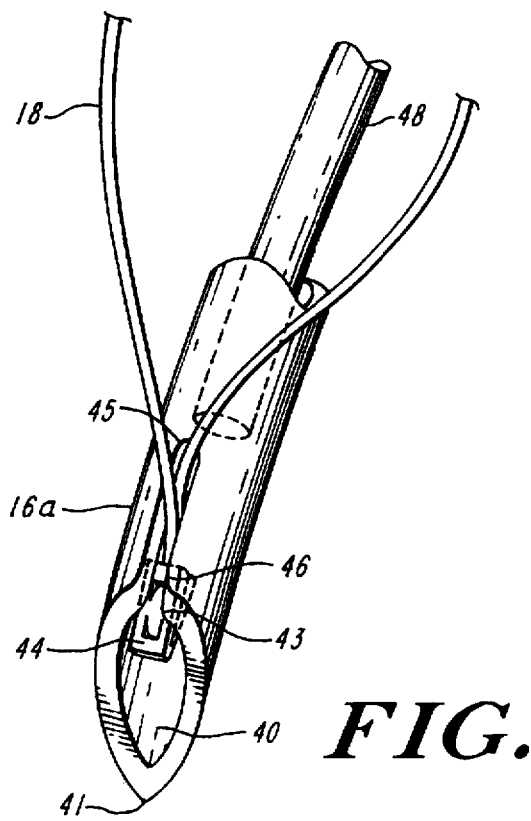
FIG. 5 is a partial view of the second suture loop and suture loop closure of FIG. 4 engaged with a suture needle.

In alternative embodiment, shown in FIGS. 4 and 5, that is particularly suited for use in closed surgical procedures the second suture loop 18 may be attached to the needle 16a by means of a suture loop closure 44. Referring now to FIG. 4, the second suture loop 18 may be formed by attaching two free ends of a length of suture thread within a suture loop closure 44. The suture loop closure 44 may consist of a metal tube having an internal diameter large enough to admit two ends of suture thread. The two free ends of the suture thread are then entered into the suture loop closure 44 and the suture loop closure 44 is crimped to retain the ends of the suture thread and form the second suture loop 18. It will be understood that the suture loop closure 40 may take other forms, including a knot tied with the two free ends of the suture thread.

A second suture loop 18, having a suture loop closure 44, may be attached to a suture needle 16a as shown in FIG. 5. In this exemplary embodiment, the suture needle 16a is a hollow member, having an open distal end 40, one wall of which includes a tissue-penetrating edge or point 41. A slot 46 is formed in the wall of the distal end of the needle, preferably opposite point 41. The slot 46 has an open end 43 that communicates with the open distal end 40 of the suture needle 16a and an opposite, closed end 45. The slot 46 is wide enough to slidably engage the second suture loop 18, but narrow enough to retain the suture loop closure 44 on one side of the slot 46. The second suture loop 18 is then attached to the suture needle 16a by placing the suture loop closure 44 inside the open first end 40 of the hollow suture needle 16a and sliding the suture loop closure 44 and the attached second suture loop 18 within the slot 46 to the closed end thereof.

The hollow suture needle 16a of FIG. 5 may also include an internally disposed actuator 48. The actuator 48 may be a rod that is selectively slidable within the hollow suture needle 16a between a first position, in which the actuator 48 is inside the hollow needle 16a and does not reach the slot 46, and a second position (not shown), in which the actuator 48 extends past the slot 46. Selectively sliding the actuator 48 from the first position to the second position causes the actuator 48 to contact the suture loop closure 44 (and the attached second suture loop 18), causing closure 44 to slide the length of slot 46 and become disengaged from the needle 16.

Suture needle 16a, as noted above, is well suited for use in closed surgical procedures. The suture needle 16a may form the distal end of an elongate suture inserter tool (e.g., an arthroscopic, laparoscopic or endoscopic tool) that is useful in closed surgical procedures.

The second suture loop 18, like the first suture loop 14, may be constructed from well known materials suitable for use as a suture. The length of the second suture loop may be determined by a person of ordinary skill in the art depending upon factors such as the dimensions of the tissue to be attached, the type of surgery to be performed, and whether an open or closed surgical technique is to be used. For example, the length of second loop 18 is generally in the range of about 20 to 40 inches, and more preferably about 30 to 36 inches for closed surgical procedures. Open surgical procedures can utilize a smaller length for second loop 18, in the range of about 6 to 12 inches and more preferably 8 to 10 inches.

It is understood that various anchor insertion tools may be used with the system of the present invention. FIG. 1 illustrates an exemplary insertion tool 20, the distal end 50 of which is removably mated with the second end 24 of the suture anchor 12. In some embodiments, the suture anchor 12 may be removably pre-mated to the distal end of the insertion tool.

The system of the invention for anchoring tissue to bone may be used in the method described hereinbelow. For purposes of illustration, FIGS. 6–10 depict the method in the context of arthroscopic shoulder repair, more specifically, attaching a detached labrum (as might result from a Bankart lesion or rotator cuff tear) to the glenoid rim of a scapula. It will be understood, however, that the system and method described herein are equally applicable to connecting detached tissue in other contexts as well.

Figure 6:
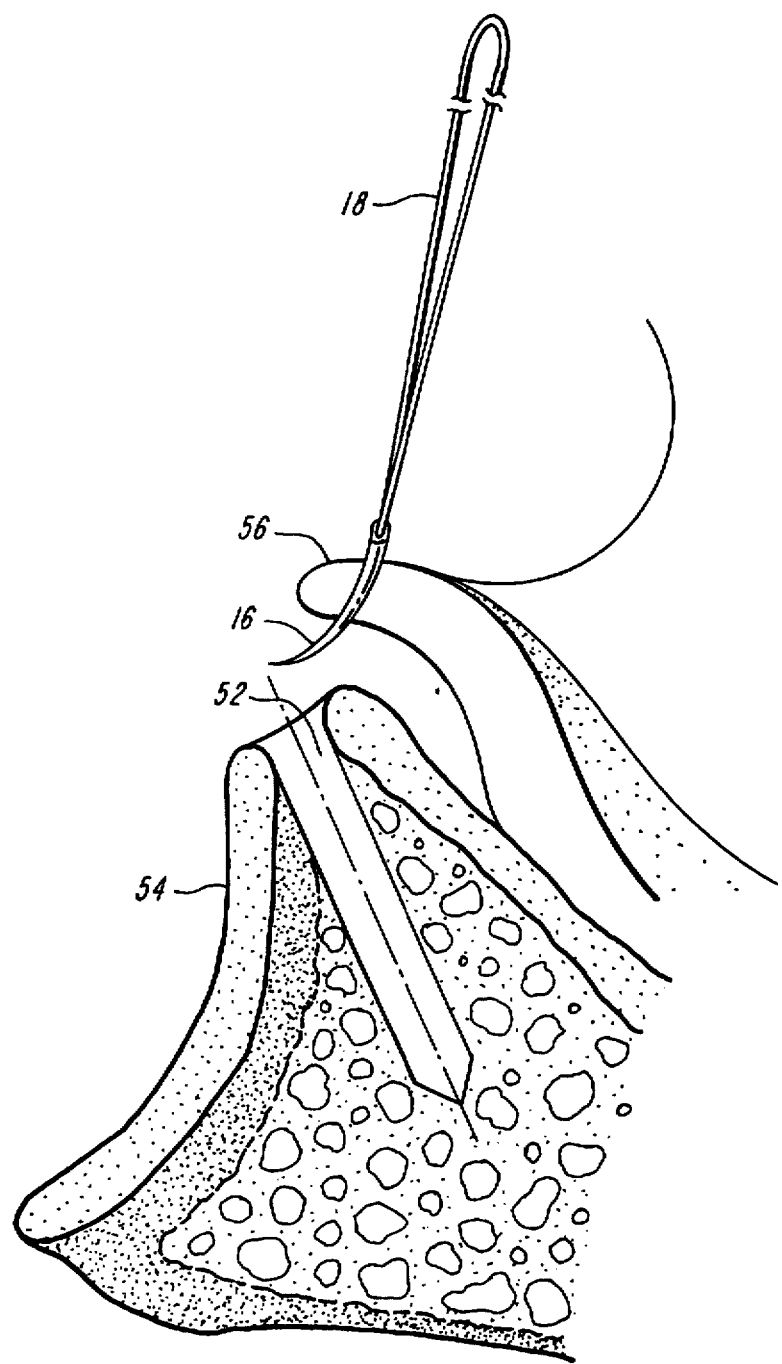
FIG. 6 is a view of a portion of the suture anchor system engaged with a detached tissue.

Referring to FIG. 6, a bore 52 is formed in a bone 54. The bore 52 must be of sufficient length to allow for adjustment of the position of the suture anchor after insertion in order to adjust the tightness of the first suture loop. The actual length of the bore 52 will depend upon the length of the first suture loop and the thickness of the detached tissue 56. The suture needle 16 is then passed through the detached tissue 56.

Figure 7:
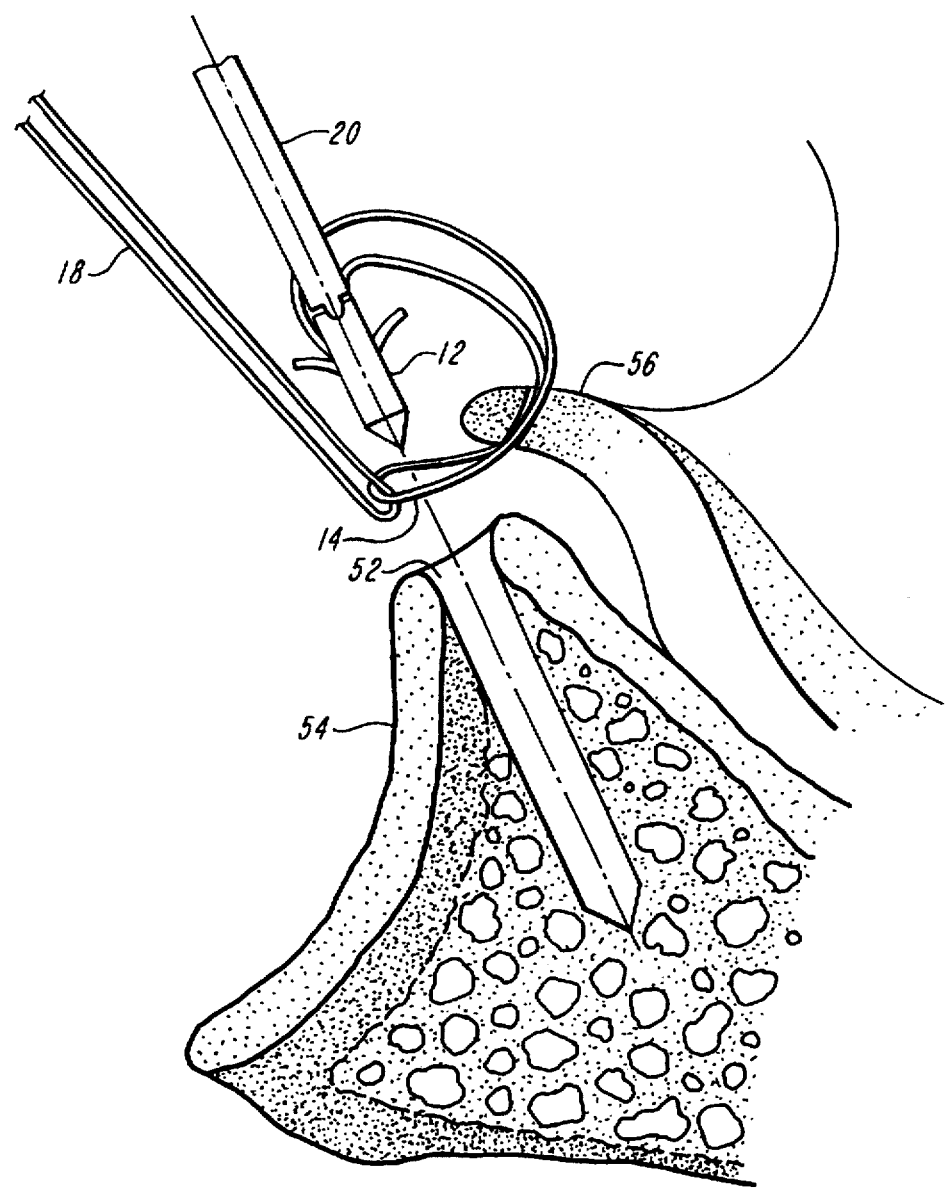
FIG. 7 is a view of a portion of the suture anchor system before the suture anchor is inserted into a bone.

Referring to FIG. 7, the suture needle 16 and the attached second suture loop 18 are pulled through the detached tissue 56 to advance the interlocked first loop 14 through the tissue. If the procedure is being performed arthroscopically, the suture needle 16a and the tool with which it is associated will be pulled from, and exit through, an exit portal (not shown).

Alternatively, in embodiments that utilize the needle 16a, shown in FIG. 5, the needle 16a may penetrate the detached tissue 56. The actuator 48 is then selectively moved so as to disengage the suture loop closure 44 and the attached second suture loop 18 from the needle 16a. The suture needle 16a may then be withdrawn from the patient's body from the portal through which the needle entered. A suture grasper or retrograder (not shown) may be used to pull the remaining portion of the second loop 18 through the detached tissue 56.

Figure 8:
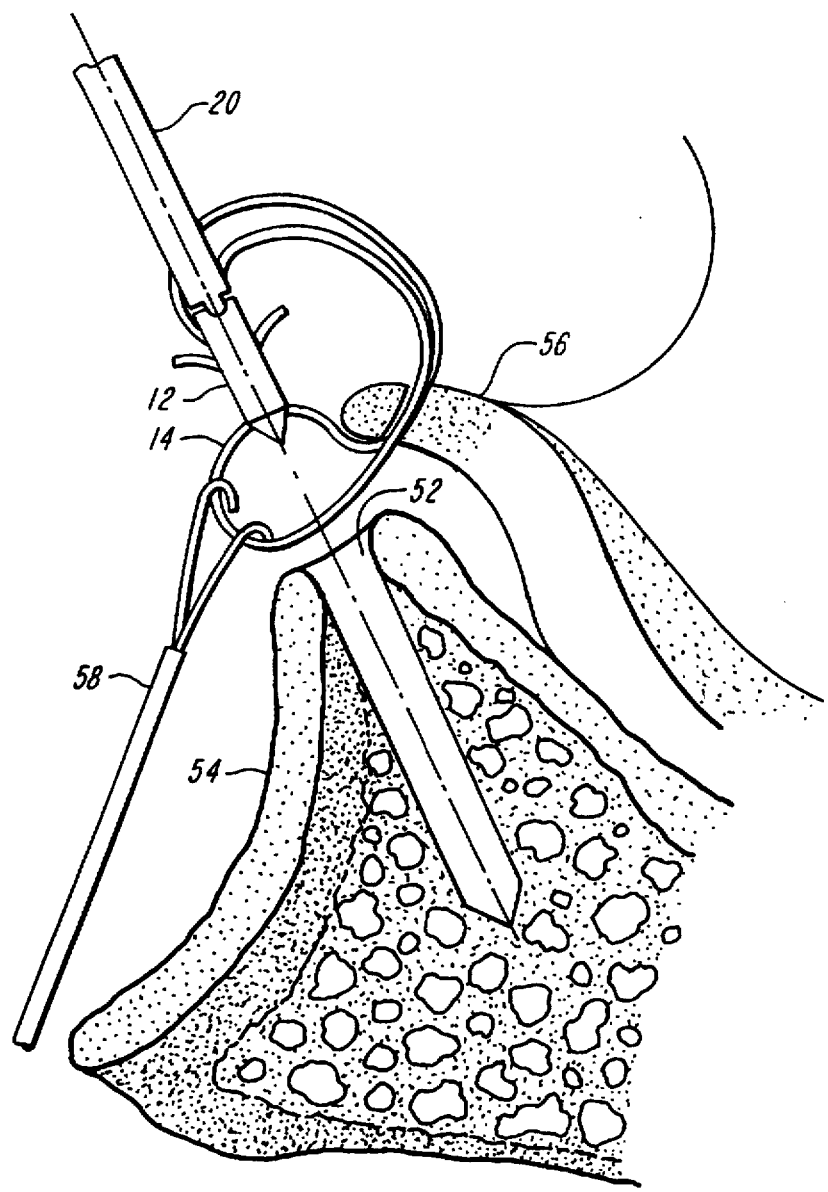
FIG. 8 is a view of a portion of the suture anchor system showing the first suture loop being positioned.

The first suture loop 14 is positioned over the bore 52 by manipulating the position of the second suture loop 18. Once the first suture loop 14 is properly positioned, the second suture loop 18 can be cut and discarded along with the suture needle 16. As shown in FIG. 8, fine positioning adjustments to the first suture loop 14 may be made using a suitable tool such as a suture retriever 58 once the second suture loop 18 is cut and discarded.

Figure 9:
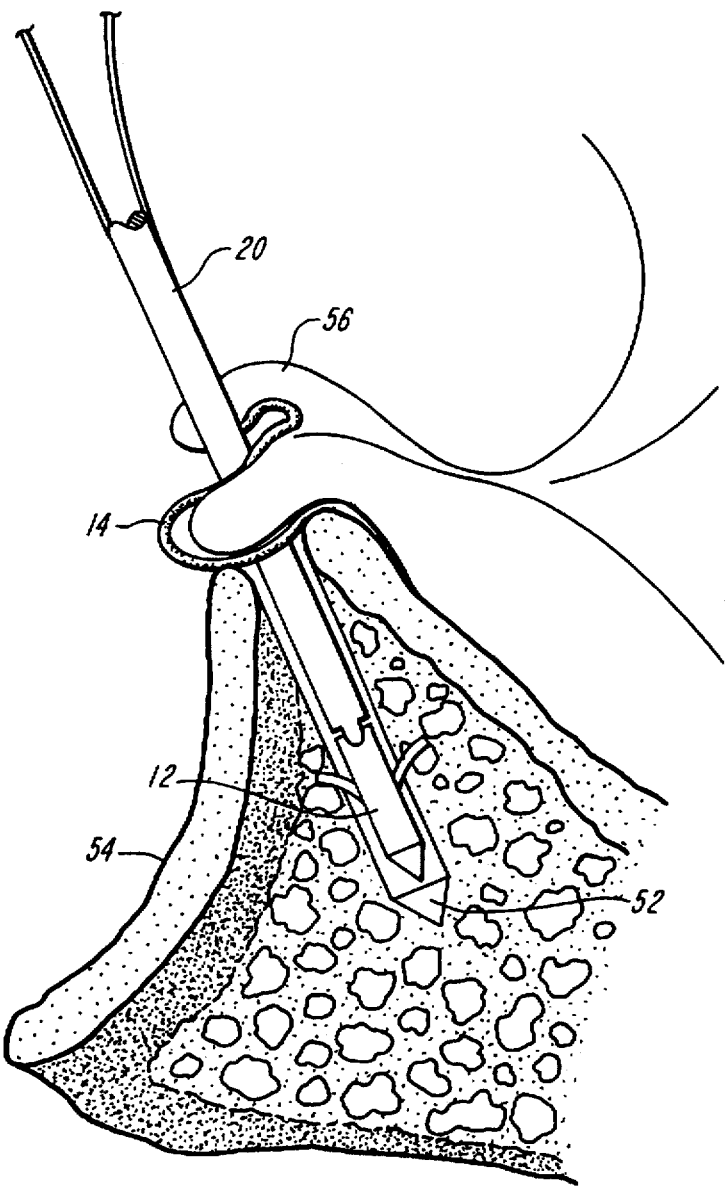
FIG. 9 is a view of a portion of the suture anchor system partially inserted into a bone.

Proper positioning of first suture loop 14 is important to enable suture anchor 12 to be passed therethrough as shown in FIGS. 8 and 9. That is, the trajectory of the suture anchor 12 is aligned with the bore 52 and the portion of the first suture loop 14 which is positioned over the bore while the suture anchor 12 is inserted through the first suture loop 14 and partially into the bore 52. Once the anchor 12 is inserted into bore 52, the insertion tool 20 may be removed.

Figure 10:
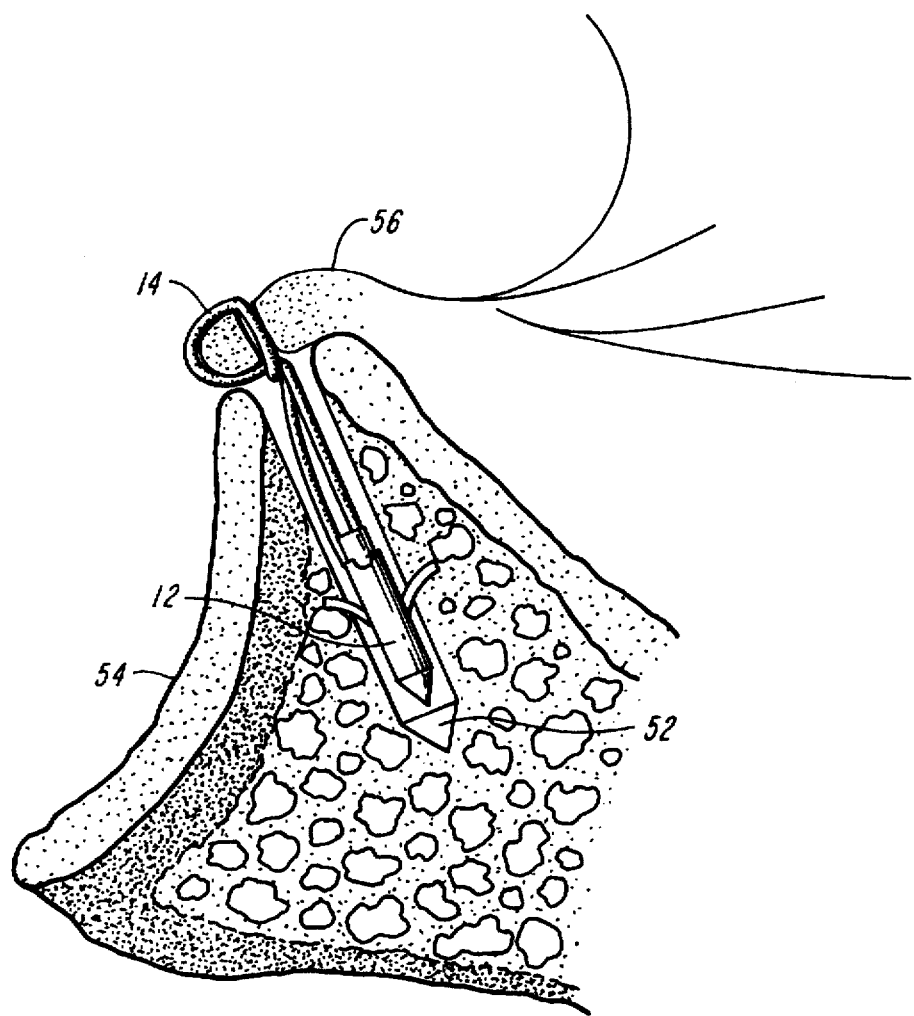
FIG. 10 is a view of a tissue attached to a bone using the system and method of the invention.

Referring to FIG. 10, when the suture anchor 12 is properly advanced into the bore 52 and set, there results a snug, anatomically correct attachment of the detached tissue 56 to the bone 54.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A system for anchoring tissue to bone, comprising:

a suture anchor having a first, bone-engaging end and a second, trailing end;

a first loop of suture thread attached to the suture anchor;

a suture needle having a first, tissue penetrating end and a second, trailing end; and a second loop of suture thread attached to the suture needle; the first and second loops of suture thread being interlocked with one another.

2. The system of claim 1, wherein the second loop comprises a suture loop closure and a length of suture thread having two free ends, the two free ends being attached to and secured within the suture loop closure.

3. The system of claim 2, wherein the suture needle comprises:

a hollow needle member having an open distal end and a proximal end, the needle member having a substantially cylindrical outer wall;

a tissue penetrating edge formed at the distal end on one portion of the outer wall; and a slot formed on the distal end, on a portion of the outer wall opposite the tissue penetrating edge, the slot having an opening communicating with the open distal end and the slot being adapted to receive and selectively secure the suture loop closure.

4. The system of claim 3, further comprising an actuator member disposed within the needle member, the actuator member being selectively slidable between a first position, wherein the actuator is located entirely within the hollow needle and does not engage the slot, and a second position, wherein the actuator extends at least to the opening of the slot so as to remove the suture closure from within the slot.

5. The system of claim 4, wherein the actuator member is an elongate rod.

6. The system of claim 1, wherein the first loop is attached to the second end of the suture anchor.

7. The system of claim 1, wherein the first loop comprises a length of suture thread having two ends, the two ends attached to each other by a suture loop closure.

8. The system of claim 7, wherein the suture anchor has a hole proximate the second end of the suture anchor, the hole having an inner diameter adapted to allow the first loop to pass through the hole while preventing the suture loop closure from passing through the hole.

9. The system of claim 1, wherein the suture anchor is substantially cylindrical and has at least one deformable barb extending from a side wall thereof.

10. The system of claim 9, wherein the suture anchor has two opposed deformable barbs extending proximally such that each barb defines an angle with a longitudinal axis of the suture anchor that is between about 10° and 90°.

11. The system of claim 9, wherein the first loop is attached to the suture anchor in proximity to the second, trailing end of the suture anchor.

12. The system of claim 1, wherein the second loop is attached to the second end of the suture needle.

13. The system of claim 12, wherein the second loop is attached to the suture needle by securing two free ends of suture thread within a hollow formed within the second end thereof.

14. The system of claim 1, further comprising a suture anchor insertion tool, the tool being in the form of an elongate member having a proximal, handle end and a distal end which is removably and replaceably matable with the second end of the suture anchor.

15. The system of claim 1, wherein the length of the second loop is in the range of about 20 to 40 inches.

16. The system of claim 1, wherein the length of the first loop is in the range of about 0.25 to 1.50 inches.

17. The system of claim 3 wherein the needle member is disposed at a distal end of a suture inserter tool.

18. A method for anchoring tissue to bone in a patient's body, comprising the steps of:

providing an anchoring system comprising a suture anchor having a first, bone engaging end and a second, trailing end, a first loop of suture thread attached to the suture anchor, a suture needle having a first, tissue penetrating end and a second end, and a second loop of suture thread attached to the suture needle, the first loop and the second loop being interlocked with one another;

forming a bore in the bone that is accessible through a portal in the patient's body;

passing the suture needle through a detached segment of tissue;

pulling the second loop completely through the detached segment of tissue so that a portion of the first loop extends through the detached segment of tissue and a portion of the first loop is positioned over the bore in the bone;

inserting the suture anchor through the portion of the first loop positioned over the bore; and installing the suture anchor within the bore such that the detached segment of tissue is reattached in a desired position through the first suture loop which is anchored within the bore.

19. The method of claim 18, wherein the second loop is detached after the anchor is inserted into the bore.

20. The method of claim 18, wherein the second loop comprises a suture loop closure and a length of suture thread having two free ends, the two free ends being attached to and secured within the suture loop closure.

21. The method of claim 20, wherein the suture needle comprises:

a hollow needle member having an open distal end and a proximal end, the needle member having a substantially cylindrical outer wall;

a tissue penetrating edge formed at the distal end on one portion of the outer wall; and a slot formed on the distal end, on a portion of the outer wall opposite the tissue penetrating edge, the slot having an opening communicating with the open distal end and the slot being adapted to receive and selectively secure the suture loop closure.

22. The method of claim 21, wherein the anchoring system further comprises an actuator member disposed within the needle member, the actuator member being selectively slidable between a first position, wherein the actuator is located entirely within the hollow needle and does not engage the slot, and a second position, wherein the actuator extends at least to the opening of the slot so as to remove the suture closure from within the slot.

23. The method of claim 22, wherein after the suture needle is passed through the detached segment of tissue, the actuator member is employed to disengage the second loop from the slot and the suture needle is withdrawn through the portal.

* * * * *